(12) United States Patent
Malin

(10) Patent No.: US 9,005,542 B2
(45) Date of Patent: Apr. 14, 2015

(54) STORAGE SYSTEM FOR STORING LABORATORY OBJECTS AT LOW TEMPERATURES

(75) Inventor: Cosmas G. Malin, Mauren (LI)

(73) Assignee: Liconic AG, Mauren (LI)

( * ) Notice: Subject to any disclaimer, the term of this patent is extended or adjusted under 35 U.S.C. 154(b) by 94 days.

(21) Appl. No.: 13/304,079

(22) Filed: Nov. 23, 2011

(65) Prior Publication Data

US 2012/0134898 A1 May 31, 2012

(30) Foreign Application Priority Data

Nov. 24, 2010 (CH) .................................. 1968/10

(51) Int. Cl.
| | |
|---|---|
| B65G 57/00 | (2006.01) |
| F25D 25/00 | (2006.01) |
| G01N 35/00 | (2006.01) |
| G01N 35/02 | (2006.01) |
| F25D 13/04 | (2006.01) |
| F25D 13/06 | (2006.01) |
| F25D 3/10 | (2006.01) |
| G01N 35/04 | (2006.01) |

(52) U.S. Cl.
CPC .......... F25D 25/005 (2013.01); G01N 35/0099 (2013.01); G01N 35/028 (2013.01); G01N 2035/0425 (2013.01); G01N 2035/00445 (2013.01); F25D 13/04 (2013.01); F25D 13/06 (2013.01); F25D 3/10 (2013.01)

(58) Field of Classification Search
CPC ........... F25D 13/04; F25D 13/06; G01N 1/42; G01N 2023/00445; A01N 1/0252
See application file for complete search history.

(56) References Cited

U.S. PATENT DOCUMENTS

| | | | |
|---|---|---|---|
| 3,272,579 A | 9/1966 | Leonard | |
| 3,782,133 A | 1/1974 | Desperier et al. | |
| 4,250,266 A | 2/1981 | Wade | |
| 4,969,336 A * | 11/1990 | Knippscheer et al. | .......... 62/266 |
| 5,192,506 A | 3/1993 | Kureshy et al. | |
| 5,226,715 A | 7/1993 | Dalatte | |
| 5,233,844 A | 8/1993 | Knippscheer et al. | |
| 5,240,139 A | 8/1993 | Chirnomas | |
| 5,345,395 A | 9/1994 | Griner | |
| 5,345,800 A | 9/1994 | Smith et al. | |
| 5,735,587 A | 4/1998 | Malin et al. | |
| 5,921,102 A | 7/1999 | Vago | |
| 6,068,393 A | 5/2000 | Hutchins et al. | |

(Continued)

FOREIGN PATENT DOCUMENTS

| | | |
|---|---|---|
| EP | 1 972 874 A2 | 9/2008 |
| EP | 1 718 545 B1 | 1/2009 |

(Continued)

OTHER PUBLICATIONS

Austrian Search Report conducted in counterpart Austrian Appln. No. CH 1968/10.

(Continued)

*Primary Examiner* — P. Kathryn Wright
(74) *Attorney, Agent, or Firm* — Greenblum & Bernstein, P.L.C.

(57) ABSTRACT

The storage arrangement has a chamber. Several Dewar flasks are arranged in the chamber and above them a picking device. The picking device has at least one cassette lift, with which storage cassettes can be removed from above from the Dewar flasks. This arrangement is suitable for storing laboratory objects at very low temperatures.

14 Claims, 10 Drawing Sheets

(56) References Cited

U.S. PATENT DOCUMENTS

| 6,129,428 | A | 10/2000 | Helwig et al. |
| 6,478,524 | B1 | 11/2002 | Malin |
| 6,694,767 | B2 | 2/2004 | Junca et al. |
| 7,314,341 | B2 | 1/2008 | Malin |
| 2001/0043031 | A1* | 11/2001 | Gonska et al. ............... 312/304 |
| 2003/0233842 | A1* | 12/2003 | Junca et al. .................... 62/266 |
| 2004/0115101 | A1 | 6/2004 | Malin |
| 2004/0213651 | A1 | 10/2004 | Malin |
| 2005/0260102 | A1 | 11/2005 | Angelantoni et al. |
| 2006/0053825 | A1* | 3/2006 | Owen et al. .................... 62/441 |
| 2006/0150659 | A1 | 7/2006 | Sidor et al. |
| 2006/0156753 | A1* | 7/2006 | Fuhr et al. ...................... 62/378 |
| 2008/0231152 | A1 | 9/2008 | Malin |
| 2008/0260511 | A1* | 10/2008 | Fattinger et al. ........... 414/788.1 |
| 2008/0272674 | A1 | 11/2008 | Malin |
| 2009/0090685 | A1 | 4/2009 | Kristensen |
| 2009/0140616 | A1 | 6/2009 | Fox |
| 2010/0183408 | A1 | 7/2010 | Malin |
| 2010/0275636 | A1* | 11/2010 | Yoshimura et al. ............. 62/374 |
| 2011/0219788 | A1* | 9/2011 | Zimmermann et al. .......... 62/63 |
| 2012/0060539 | A1* | 3/2012 | Hunt et al. ...................... 62/336 |
| 2012/0102983 | A1* | 5/2012 | Parmegiani ....................... 62/62 |

FOREIGN PATENT DOCUMENTS

| JP | 2005-143873 | 6/2005 |
| WO | 97/48309 A1 | 12/1997 |
| WO | 98/43592 | 10/1998 |
| WO | WO 2010057589 A1 * | 5/2010 |

OTHER PUBLICATIONS

European Search Report/Office Action conducted in related European Appln. No. 120 08 284.7-1602 (May 13, 2013).

\* cited by examiner

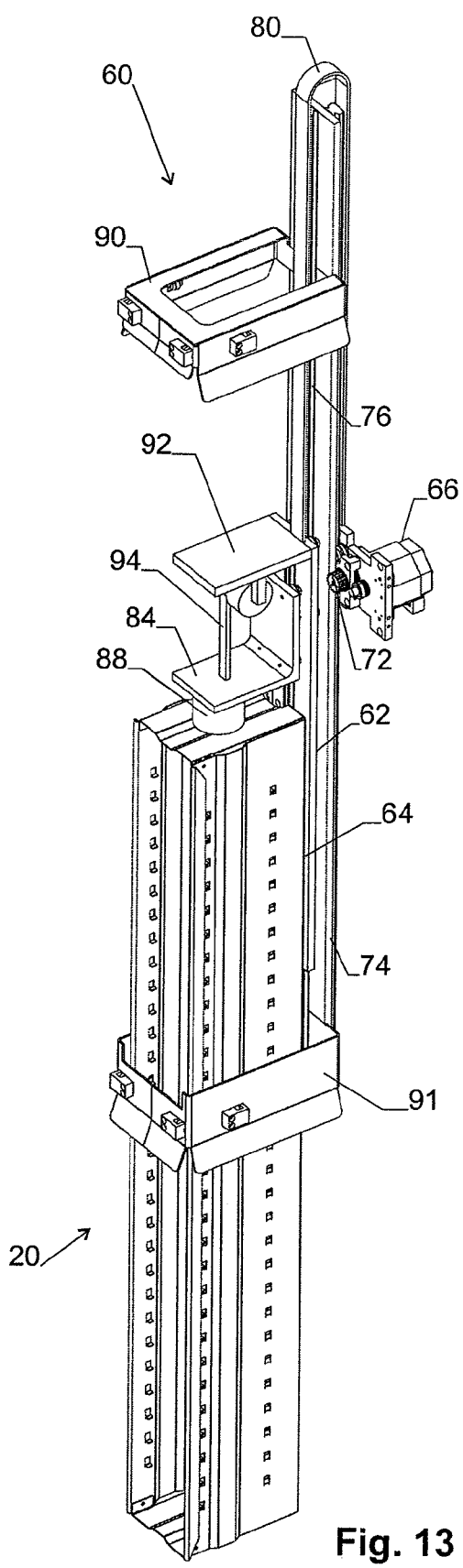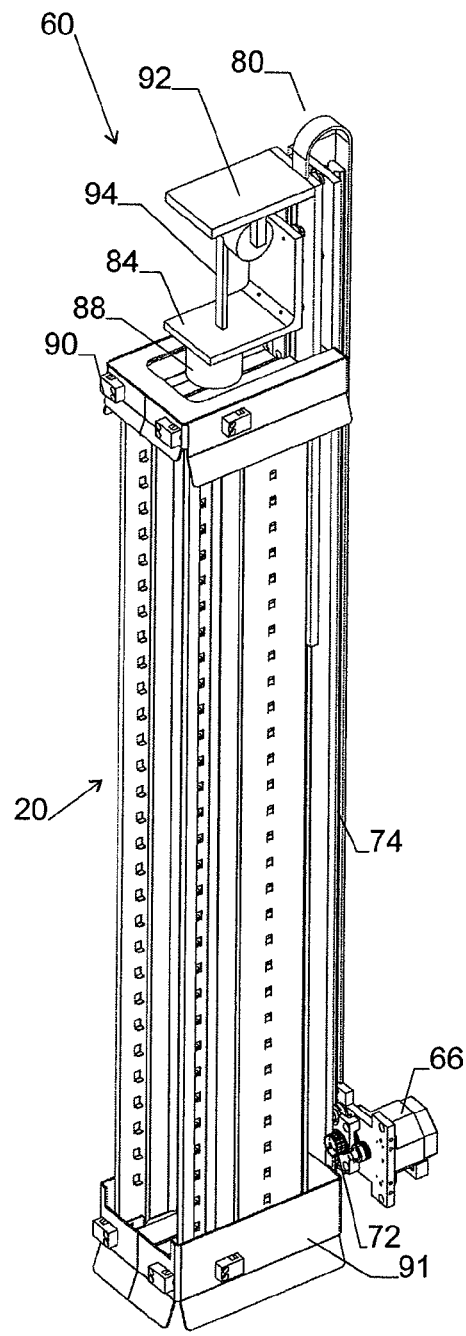
Fig. 13
Fig. 14

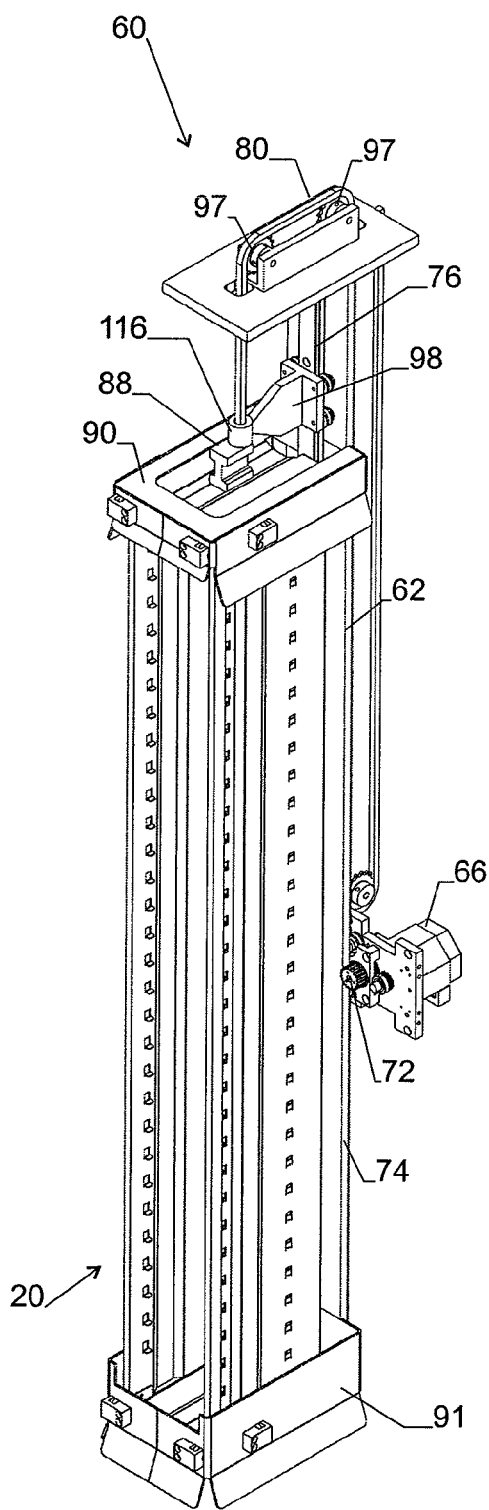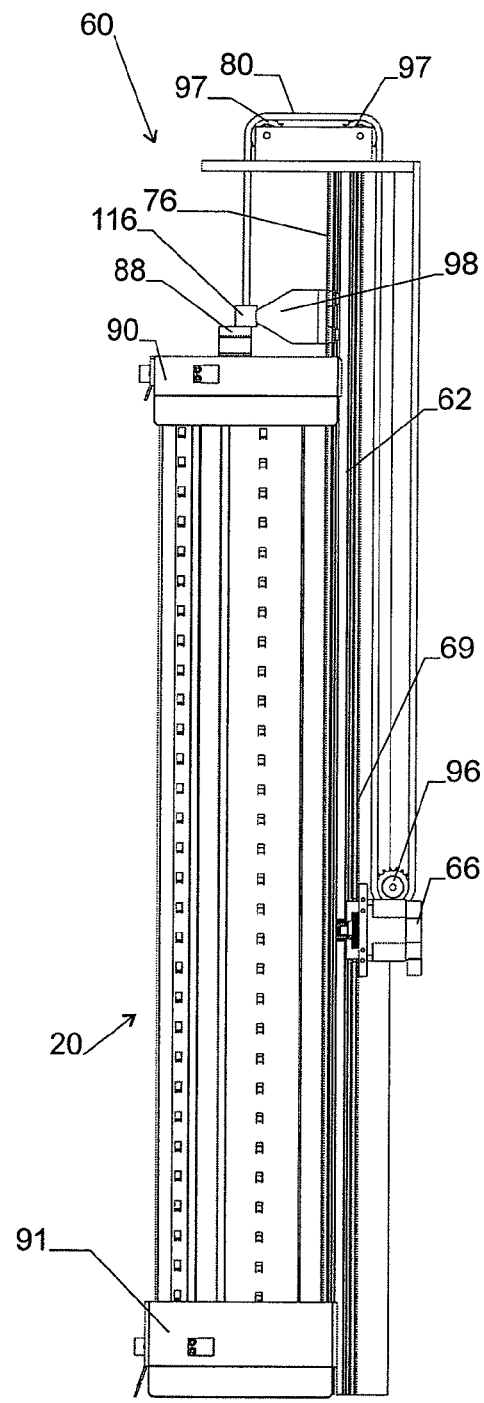
Fig. 17
Fig. 18

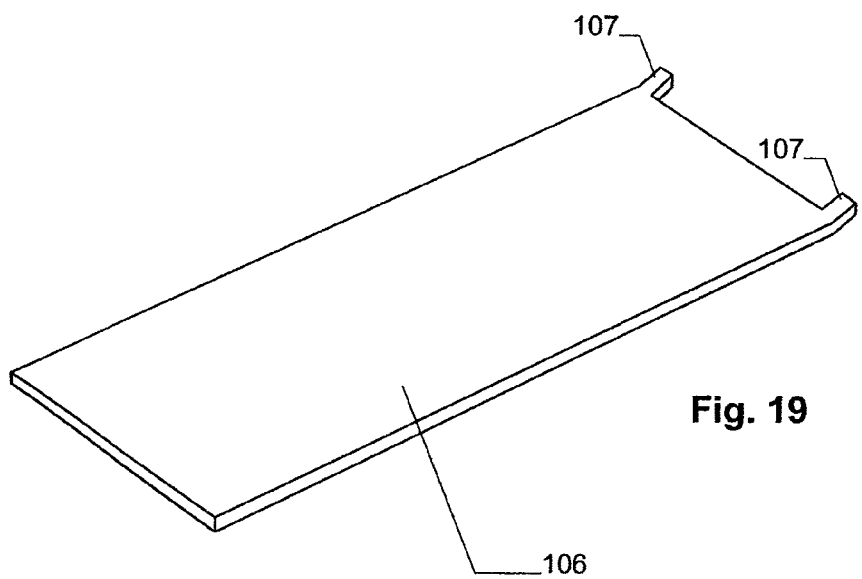
Fig. 19
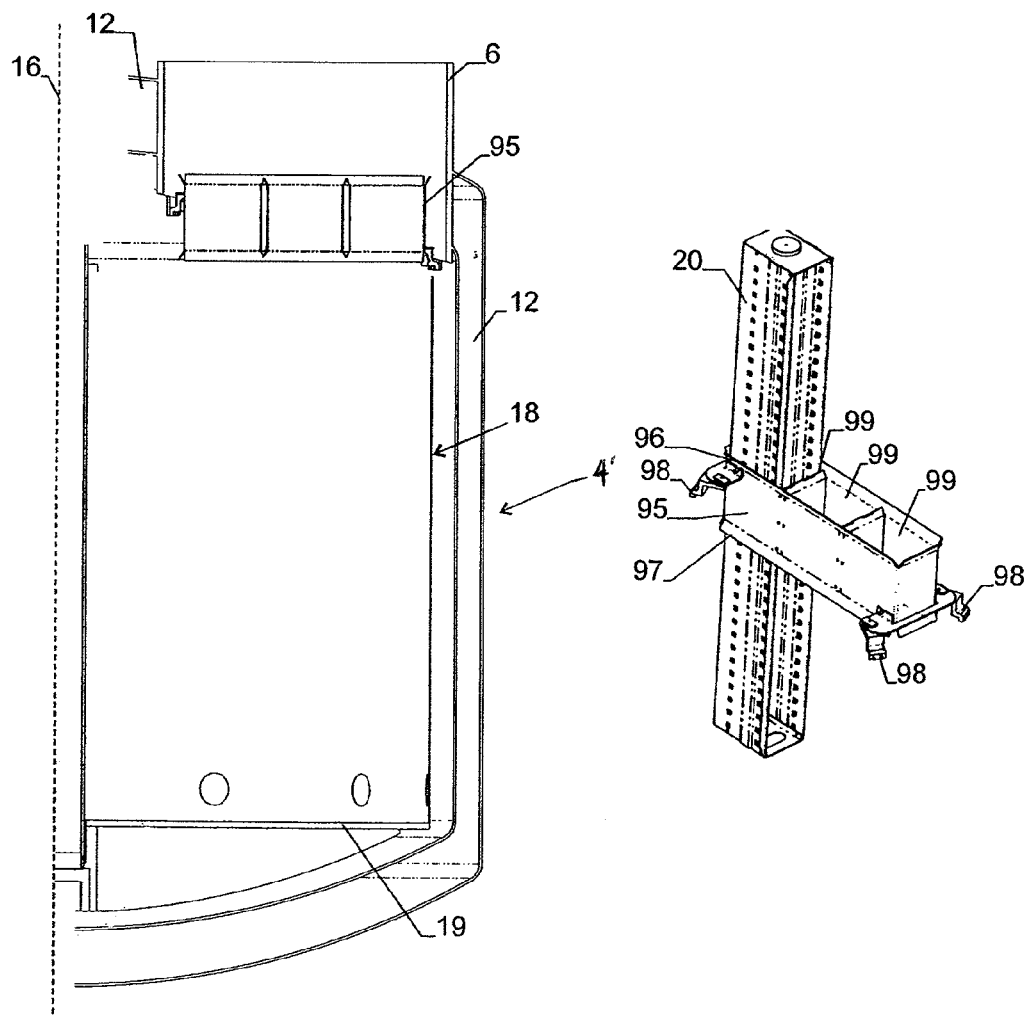
Fig. 20
Fig. 21

US 9,005,542 B2

STORAGE SYSTEM FOR STORING LABORATORY OBJECTS AT LOW TEMPERATURES

CROSS-REFERENCE TO RELATED APPLICATIONS

The present application claims priority under 35 U.S.C. §119 of Swiss Patent Application No. CH-1968/10 filed Nov. 24, 2010, the disclosure of which is expressly incorporated by reference herein in its entirety.

BACKGROUND OF THE INVENTION

1. Field of the Invention

The invention relates to a storage arrangement for storing laboratory objects at very low temperatures.

2. Discussion of Background Information

The storage of laboratory objects at very low temperatures, such as temperatures below 160° C., for example, typically at −196° C., is very complex and automation is difficult to achieve. A storage arrangement for low temperatures is known from EP 1 972 874, but this system is suitable for really low temperatures only to a limited extent.

SUMMARY OF THE EMBODIMENTS

Embodiments of the invention provide a storage arrangement of the type mentioned at the outset, which can be operated automatically.

Accordingly, embodiments are directed to the storage arrangement for storing laboratory objects that includes a chamber, at least one Dewar flask arranged in the chamber for storing the laboratory objects at a storage temperature $Ts<Tc$. The temperature Tc is a temperature of the chamber. The storage arrangement also includes several storage cassettes arranged in the Dewar flask, in which each storage cassette forms a plurality of storage sites arranged one above the other for accommodating the laboratory objects, and a picking device that is arranged in the chamber in a moveable manner above the Dewar flask or Dewar flasks and has at least one cassette lift in order to remove storage cassettes in the vertical direction from the Dewar flasks and to insert them therein again.

According to embodiments, the storage arrangement thus has

A chamber that preferably can be kept at a chamber temperature $Tc<0°$ C.

At least one Dewar flask, in particular several Dewar flasks. Vessels of this type are able to store objects even at extremely low temperatures without high energy consumption. The Dewar flasks are embodied to store the laboratory objects at a storage temperature $Ts<Tc$, wherein Tc is the chamber temperature.

Storage cassettes: several storage cassettes are arranged in each Dewar flask. Each storage cassette forms a plurality of storage sites arranged one above the other to accommodate laboratory objects. One laboratory object, or also several, can be stored for each storage site.

A picking device, which is arranged in the chamber above the Dewar flask or the Dewar flasks and is used for the automatic picking of the laboratory objects. It has at least one cassette lift, in order to remove storage cassettes in the vertical direction from the Dewar flasks and to replace them therein.

Due to this embodiment it is possible to provide an automated storage arrangement for very low temperatures. The energy consumption by the system is reduced because the actual storage temperature is maintained only inside the Dewar flasks. As the picking device is arranged outside the Dewar flasks, in the chamber, the components thereof are not exposed to extremely low temperatures and at the same time, large differences in temperature and ice formation are avoided. The arrangement above the Dewar flasks and the vertical access to the storage cassettes reduce the heat equalization between the chamber and the interior of the Dewar flasks.

Advantageously, a door is provided on the top of the at least one Dewar flask, which door can be automatically opened and closed. When the door is opened, the picking device can access the storage cassettes in the Dewar flask from above.

Several Dewar flasks, which can be charged by the picking device, can be provided in the chamber. This has the advantage that smaller, more inexpensive Dewar flasks can be used.

If several Dewar flasks are provided, advantageously a common picking device is provided for all of the Dewar flasks, i.e. exactly one picking device is provided, which operates all of the Dewar flasks.

The cassette lift can have several telescopic sections that can be extended with respect to one another in a telescopic manner, a pulley and/or a belt or a chain, in order to lower a gripper device for gripping the storage cassettes into the at least one Dewar flask. The vertical installation height of the cassette lift can be reduced by the use of a telescopic solution or pulley solution so that the installation height of the chamber above the Dewar flasks can be kept low.

Furthermore, at least one centering element can be provided at a fixed height, into which a storage cassette can be moved in order to align the storage cassette horizontally. A storage cassette aligned in this manner can be loaded and unloaded better.

The centering element can be part of the cassette lift. Alternatively, the centering element can also be arranged on the Dewar flask.

Furthermore, the picking device can have a handling device, which has a vertically moveable scoop that can be extended horizontally into a raised storage cassette, with which scoop objects can be removed from the storage cassette or can be inserted therein. In the event that the picking device has two cassette lifts, the handling device is advantageously arranged between the two cassette lifts, so that both of them can be served thereby.

Furthermore, it is advantageous to arrange in the chamber at least two rows of Dewar flasks rotated by 180° with respect to one another and to arrange the cassette lifts likewise rotated by 180° with respect to one another. In this case respectively one cassette lift is correctly aligned with respect to the Dewar flasks in one row.

The picking device advantageously has a carriage that can be moved horizontally in two directions, on which the at least one cassette lift is arranged, so that the cassette lift can be moved above each desired Dewar flask and/or plates picked or to be picked or laboratory objects can be conveyed to a transfer station at the edge of the chamber. In this case the carriage can be connected to the housing via a first and a second rail, wherein the two rails are perpendicular to one another and are arranged higher than the Dewar flask or the Dewar flasks.

Advantageously, a rotatable carousel is provided in each Dewar flask on which carousel the storage cassettes are arranged. Each storage cassette can thereby be brought into the active area of the picking device. Furthermore, a carousel is particularly suitable for installation in the normally round Dewar flasks. To improve the utilization of space, the storage cassettes are advantageously arranged in several concentric circles around a rotational axis of the carousel.

The picking device can also have a sample removal device, with which an individual laboratory object can be removed from a sample plate removed from a storage cassette or inserted into the sample plate. In this manner in the case of a sample plate which holds several laboratory objects, only one can be removed. The paths are thereby shorter and the other laboratory objects can be quickly returned to the Dewar flask.

Embodiments of the invention are directed to a storage arrangement for storing laboratory objects that includes a chamber and at least one Dewar flask positionable in the chamber that is structured and arranged to store the laboratory objects at a storage temperature Ts<Tc, in which Tc is a temperature of the chamber. The storage arrangement also includes a plurality of storage cassettes positionable in the at least one Dewar flask, each storage cassette including a plurality of storage sites arranged one above the other for accommodating the laboratory objects, and a picking device structured and arranged for movement in the chamber above the at least one Dewar flask and having at least one cassette lift structured and arranged to selectively remove storage cassettes from the at least one Dewar flask and to place storage cassettes into the at least one Dewar flask.

According to embodiments, the at least one cassette lift is further structured and arranged to selectively remove and place the storage cassettes in a vertical direction.

In accordance with other embodiments of the invention, a lid can be located on a top of the at least one Dewar flask that is structured and arranged to provide access from above to storage cassettes in the at least one Dewar flask. The lid may be structured to be opened automatically.

According to still other embodiments, the chamber can be a cooling chamber having a cooling device structured and arranged to produce a chamber temperature Tc<0° C.

Further, the at least one Dewar flask may include several Dewar flasks positionable arranged in the chamber, and the picking device may be common to the several Dewar flasks to selectively remove and place storage cassettes respectively from and into the several Dewar flasks.

In accordance with further embodiments, the cassette lift may include one of a chain or a belt and a gripper device coupled to the one of a chain or belt that is structured and arranged to be lowerable into the at least one Dewar flask and to grip a selected storage cassette. The one of a chain or belt may be arranged in a pulley. Further, the one of a chain or belt can be deflected by the pulley, which may include at least one vertically stationary roller and at least one roller that is displaceable in a vertical direction via a vertical drive.

According to still other embodiments of the instant invention, the cassette lift may include an electromagnet structured and arranged as a gripper device to magnetically retain the storage cassettes.

In accordance with further embodiments of the invention, at least one centering element can be positionable at a fixed height and may be structured and arranged to receive a selected storage cassette in order to horizontally align the storage cassette. The at least one centering element can include at least two centering elements arranged spaced apart and one above the other to receive a raised storage cassette. Moreover, the raised storage cassette, positioned in a region of an upper element of the at least two centering elements and in a region of a lower element of the at least two centering elements, can be horizontally movable. The cassette lift can include the at least one centering element. Still further, the at least one centering element may be structured and arranged on the at least one Dewar flask, and can include several guide openings for respectively accommodating one storage cassette. The at least one centering element may be structured and arranged in an opening of the at least one Dewar flask.

According to still other embodiments of the invention, the picking device may include a handling device having a scoop that is vertically movable and horizontally extendable into a raised storage cassette. The at least one cassette lift may include two cassette lifts, and the handling device can be located between the two cassette lifts. The at least one Dewar flask may include a plurality of Dewar flasks arranged in at least two rows, such that the Dewar flasks of one row may be positionable to be oriented 180° to the Dewar flasks in another row, and the two cassette lifts may be positionable to be oriented 180° to one another. Further, at least one holder element can be structured and arranged at an end of the scoop in an upward direction that may be insertable into the storage cassettes to secure the laboratory objects on the scoop. The storage cassettes can have a back wall structured so that a spacer, which is formed in at least one first region, may delimit at least one second region of the back wall that can be one of open or set back to provide the at least one holder element access behind the laboratory object.

According to other embodiments, the picking device may include a carriage structured and arranged for horizontal movement in two directions, and the cassette lift may be arranged on the carriage. Further, a first and second rail may be located within the chamber above the at least one Dewar flask to which the carriage is connectable, and the first and a second rail can be oriented perpendicular to one another.

In accordance with still yet other embodiments of the present invention, a housing may be structured and arranged to surround the chamber.

BRIEF DESCRIPTION OF THE DRAWINGS

Further embodiments, advantages and applications of the invention are shown by the dependent claims and the now following description based on the figures. They show:

FIG. 13 the cassette lift from FIG. 12 in the center position;

FIG. 14 the cassette lift from FIG. 12 in the raised position;

FIG. 17 the cassette lift from FIG. 15 in raised position;

FIG. 18 a side view of the cassette lift from FIG. 17;

FIG. 19 the scoop from FIG. 10 in detail;

FIG. 20 a partial section through a second embodiment of a Dewar flask; and

FIG. 21 a storage cassette with a second embodiment of the centering element.

DETAILED DESCRIPTION OF THE EMBODIMENTS

Figure 1:
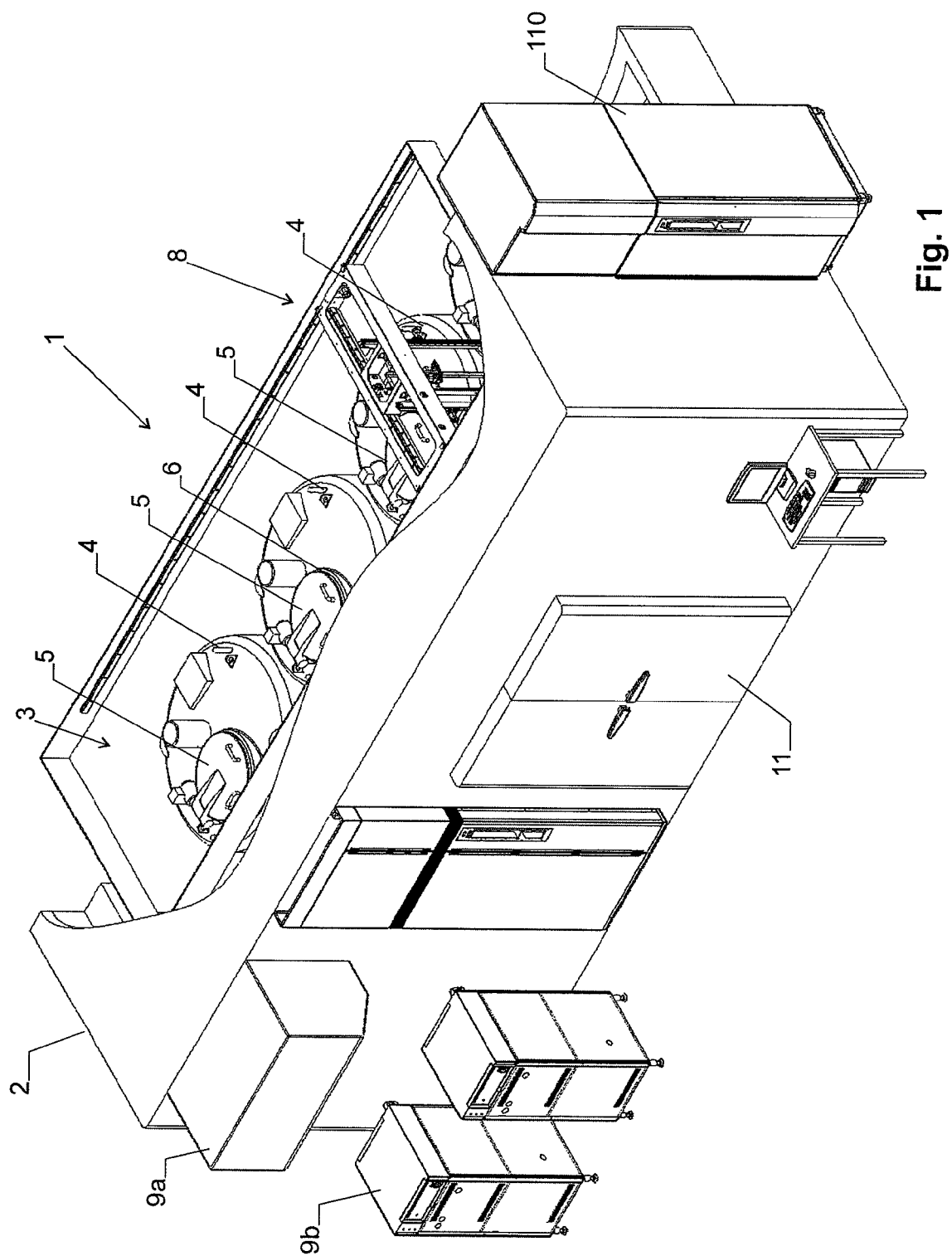
FIG. 1 a view of a storage arrangement, wherein the outer walls are shown only in part.
Figure 2:
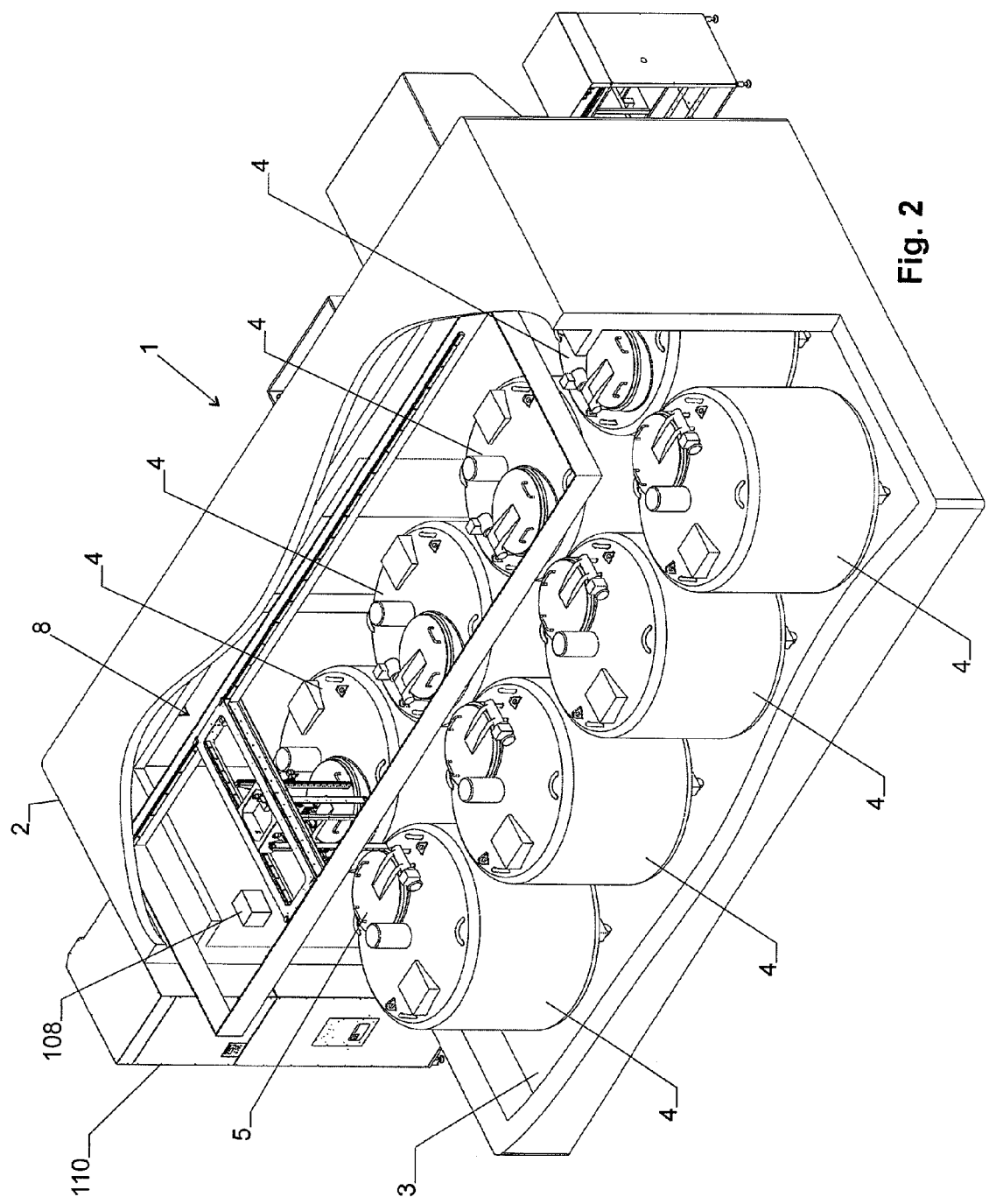
FIG. 2 a second view of the storage arrangement from FIG. 1.

Storage Arrangement:

FIGS. 1 and 2 show a storage arrangement 1 for the long-term storage of samples at very low temperatures, in particular a storage temperature Ts below 160° C., typically at −196° C. The storage arrangement is designed to deposit and retrieve the samples automatically and to move them inside the storage arrangement between different storage positions. Arrangements of this type have to meet high requirements regarding the safety of the samples, reliability and energy efficiency.

The samples are contained, for example, in sample tubes, which in turn are arranged in plates. Several of these sample plates are respectively stored one above the other in a storage cassette.

The storage arrangement has an insulated outer housing 2, which surrounds a chamber 3. At least one Dewar flask 4 is arranged in the chamber 3. Preferably, several such Dewar flasks 4 are provided. Each Dewar flask 4 has in a known manner an evacuated, mirrored insulation wall, which has low thermal conduction. The Dewar flasks 4 are closed on all sides in the embodiment shown and for access in each case a lid 5 is provided on their inside. The lid 5 covers an opening 6 arranged on the top of the Dewar flask 4.

The chamber 3 is preferably embodied as a cooling chamber. The Tc of the chamber 3 is advantageously lower than 0° C., in particular lower than −20° C. or −50° C. This lowering of the temperature prevents ice formation in the Dewar flasks 4 or on the samples. The storage temperature Ts in the Dewar flasks 4 is lower than the chamber temperature Tc and is preferably at the referenced "very low temperatures", i.e., typically at −196° C.

However, a cooling of the chamber 3 is not absolutely necessary. The chamber 3 can also e.g., contain only a defined atmosphere (for example, dry air or nitrogen atmosphere), or it can be a not specially air-conditioned storage space.

Furthermore, a picking device 8 is arranged in the chamber 3. This picking device 8 has one transport device each for the storage cassettes, the sample plates and the sample tubes. It is arranged in a moveable manner above the Dewar flasks 4. As can be seen from FIGS. 1 and 2, advantageously precisely one picking device 8 is provided, which serves all of the Dewar flasks.

The storage arrangement furthermore comprises a first cooling device 9a for producing the interior temperature Ti in the chamber 3 as well as a second cooling device 9b for producing the storage temperature Ts in the Dewar flasks 4.

The chamber 3 is accessible via a door 11, which is large enough to accommodate the Dewar flasks 4.

Figure 3:
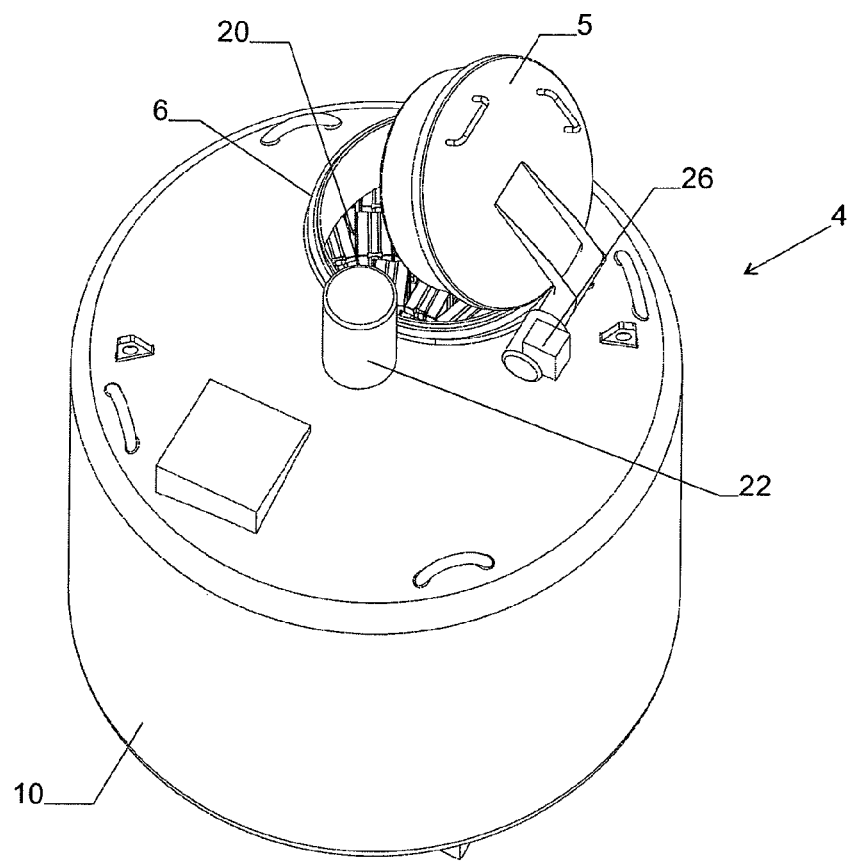
FIG. 3 a view of a Dewar flask.
Figure 4:
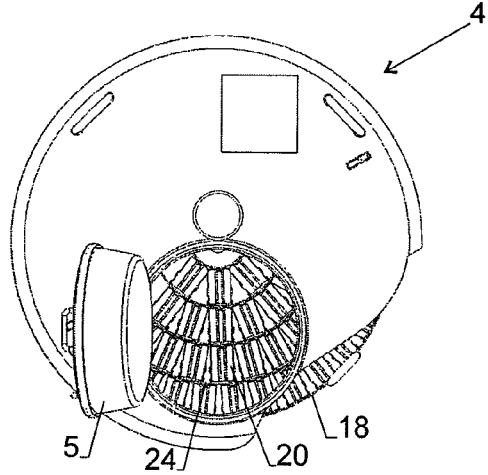
FIG. 4 the Dewar flask from FIG. 3 from above, with partially removed wall.
Figure 5:
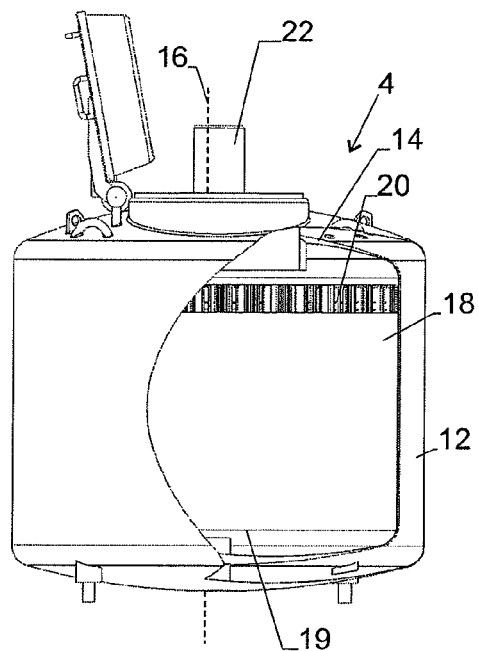
FIG. 5 the Dewar flask from FIG. 4 from the side.

Dewar Flasks:

A first embodiment of a Dewar flask 4 is shown in FIGS. 3-5. It has an essentially cylindrical housing 10, in which the above-mentioned vacuum insulation 12 is arranged. The vacuum insulation 12 surrounds an inner space 14, which accommodates a carousel 18 that can be rotated about a vertical rotational axis 16. The carousel 18 bears on a base plate 19 a plurality of storage cassettes 20.

A positioning drive 22 is used to rotate the carousel 18 around the rotational axis 16 and to bring it into defined positions.

The storage cassettes 20 are arranged in several concentric circles around the rotational axis 16, positioned radially by vertical walls 24 and are moveable in the vertical direction.

The lid 5 can be automatically opened and closed with a door drive 26. It is arranged on the top of the Dewar flask 4 and positioned and dimensioned such that when the lid 5 is opened, each storage cassette 20, which has been rotated with the positioning drive 22 into the region of the door opening 6, can be drawn out from above. Preferably, the horizontal diameter of the door opening 6 is smaller, however, than half the horizontal diameter of the Dewar flask 4 so that an excessive loss of cooling can be avoided when opening the lid 5.

A second embodiment of a Dewar flask 4' is shown in FIG. 20. In particular the double wall with the vacuum insulation 12 as well as the opening 6 closed by the lid 5 (not shown) can be seen in FIG. 20. In turn a carousel 18 is located in the interior of the Dewar flask, which carousel bears on its base plate 19 a plurality of storage cassettes (not shown).

In the embodiment according to FIG. 6, a centering element 95 is arranged in the opening 6, the function of which centering element is explained below.

Figure 6:
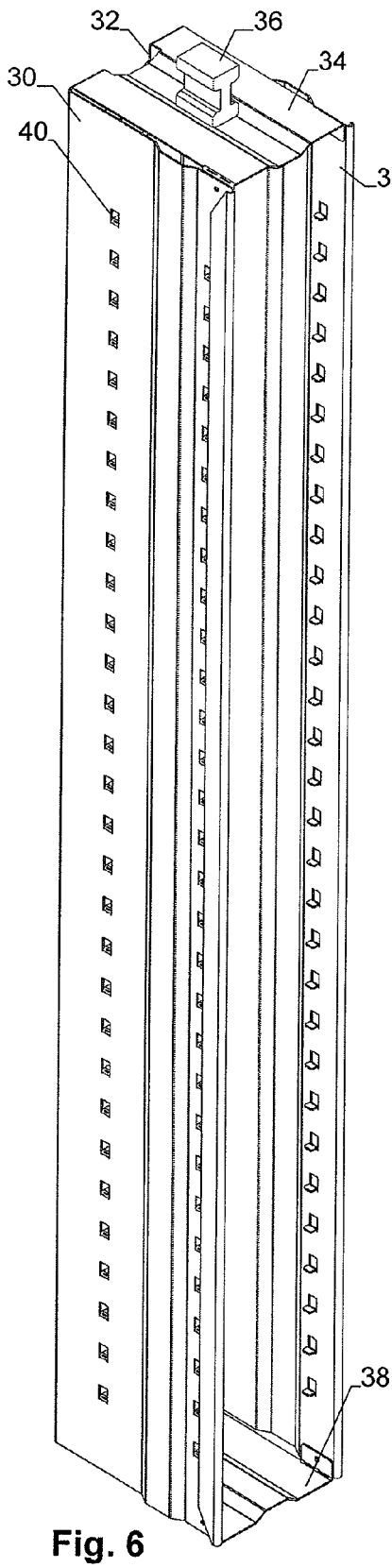
FIG. 6 a storage cassette.
Figure 7:
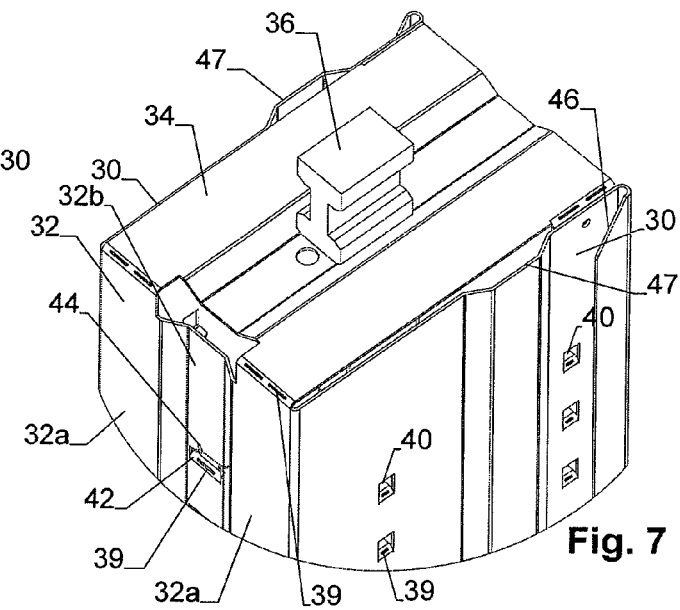
FIG. 7 the upper end of the storage cassette from FIG. 6.
Figure 8:
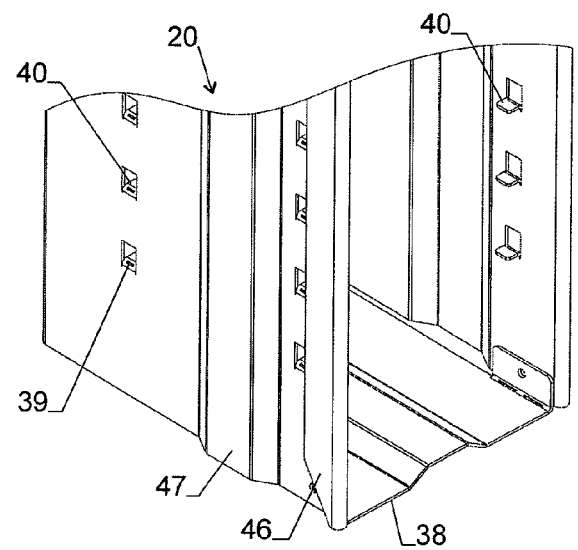
FIG. 8 the lower end of the storage cassette from FIG. 6.

Storage Cassettes:

FIGS. 6-8 show an advantageous storage cassette 20. It has two parallel, vertical side walls 30 and perpendicular thereto a vertical back wall 32. The storage cassette is open opposite the back wall 32 so that access to the sample plates accommodated in the storage cassette is possible. A top part 34 is arranged at the upper end of the storage cassette 20, to which top part the side walls 30 and the back wall 32 as well as a handle 36 projecting upwards are attached. The handle 36 is used for the picking device described below for gripping the cassette. At the lower end of the storage cassette 20 a base part 38 is arranged to which in turn the side walls 30 and the back wall 32 are attached.

The storage cassette forms a plurality of storage sites arranged one above the other, each of which can accommodate a sample plate. They are structured such that they ensure a high mechanical precision over a very wide temperature range. Furthermore, they have centering and transport devices, which render possible a high mechanical positioning precision and automatic transport.

In the exemplary embodiment shown each storage site is formed by several angle brackets 40, 42. These angles project inwards from the side walls 30 (angle bracket 40) or the back wall 32 (angle bracket 42) and form lateral and rear supports for the sample plates. The angle brackets 42 on the back wall 32 have on their front edge retention elements 44 (see FIG. 7) turned up, i.e., bent upwards, which engage in the inserted sample plate, e.g., behind a back wall of the same, in order to thus prevent them from slipping out towards the front.

Figure 9:
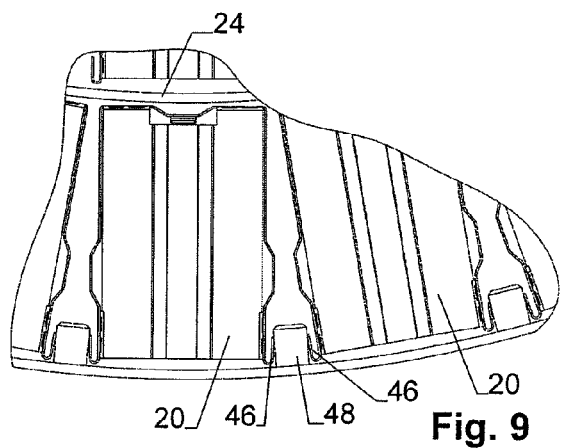
FIG. 9 the arrangement of storage cassettes in a Dewar flask.

The side walls 30 of the storage cassettes 20 are bent upwards at the front and thus form bent-up regions 46, with which the storage cassette 20 is positioned laterally in the Dewar flask 4. As shown in FIG. 9, the bent-up regions 46 in each case bear laterally against a holder element 48 arranged in a stationary manner in the carousel 18. The bent-up regions 46 increase the stability of the storage cassettes. For the same reason a vertical bead 47 runs in each side wall.

As can be seen in particular from FIG. 7, the side walls 30 and the back wall 32 are formed by bent-up sections of a single piece of sheet metal. Advantageously, the lid part 34 and the base part 38 are also formed by bent-up sections of the same piece of sheet metal. The angle brackets 40, 42 can also be formed by bent-up sections of the sheet metal part. The production of the storage cassette is thus simplified and the storage cassette is tough and temperature-resistant.

Predetermined bending locations 39 are provided between at least one part of the bent-up sections of the piece of sheet metal, in particular in the form of elongated holes or slots, which facilitate a locationally precise bending of the piece of sheet metal during production.

Advantageously, the outline of the piece of sheet metal is cut by laser processing and the predetermined bending locations 39 are also produced with the laser in the same step so that a high relative positioning accuracy is ensured.

The storage cassette shown is suitable not only for use in the storage arrangement described here, but also for use for other purposes, e.g., in general for storage of laboratory objects (such as, e.g., microtitration plates) inside and outside climate-controlled cabinets.

Figure 10:
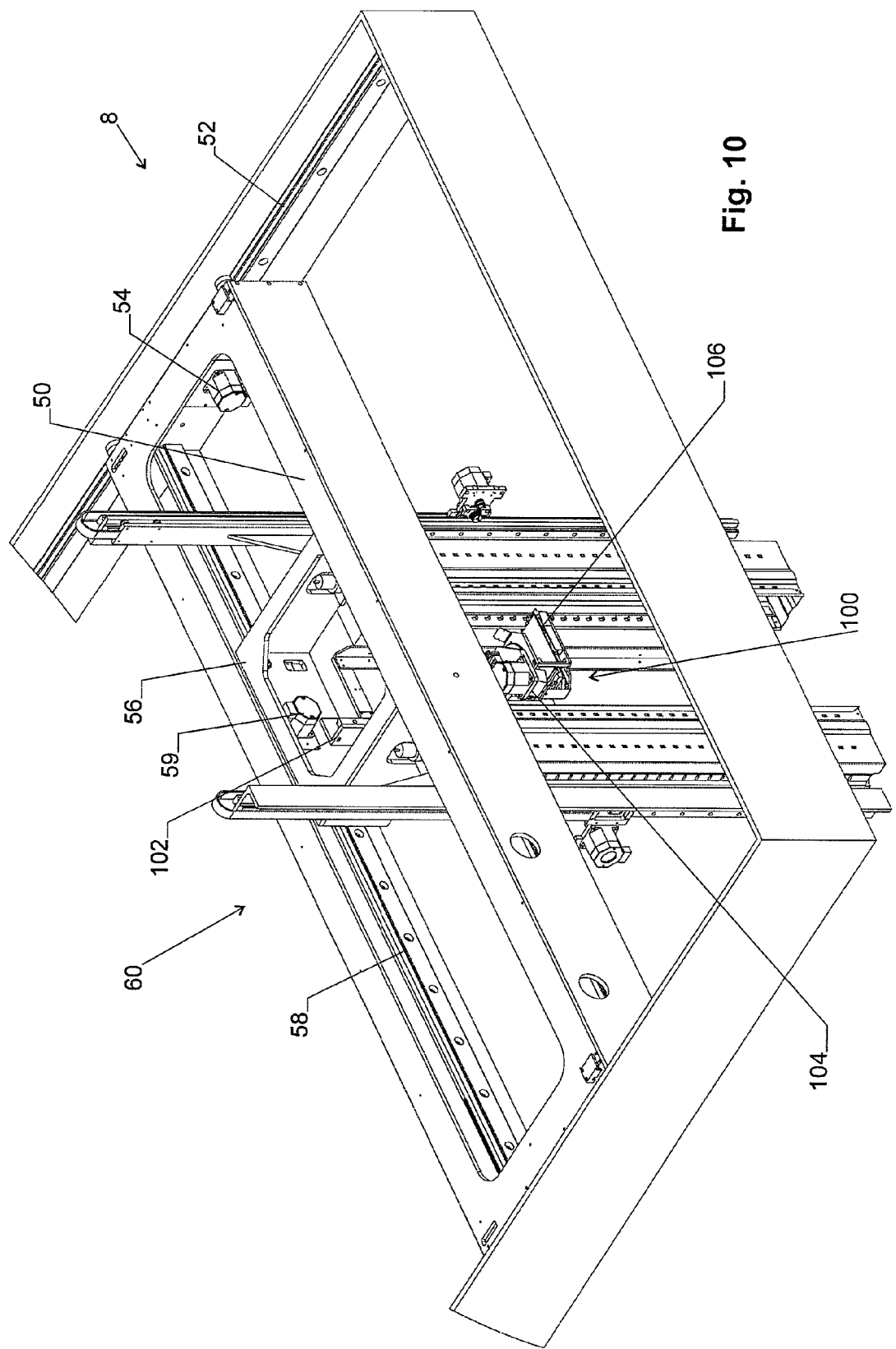
FIG. 10 a picking device.

Picking Device:

The picking device 8 is shown in more detail in FIG. 10. It has a car 50, which can be moved horizontally along a first rail 52 arranged in a stationary manner in the storage arrangement 1, for which purpose a first horizontal drive 54 is provided. A carriage 56 is arranged in the car 50, which carriage can be moved horizontally along a second rail 58, which is arranged on the car 50 perpendicular to the first rail. To this end, a second horizontal drive 59 is provided. In this manner the carriage 56 can be moved horizontally in all directions.

At least one cassette lift 60 is arranged on the carriage 56, with which cassette lift storage cassettes can be removed from the Dewar flasks 4 in the vertical direction and inserted therein again.

In the embodiment according to FIG. 10 two such cassette lifts 60 are provided. They are mounted rotated by 180° to one another. This arrangement was selected because in the embodiment according to FIGS. 1 and 2 the Dewar flasks are also arranged in two rows rotated by 180° to one another so that a correspondingly oriented cassette lift 60 is available for each row of Dewar flasks. Alternatively to this, only a single cassette lift 60 could also be provided, which can be rotated by 180° about a vertical axis. Or the Dewar flasks 4 can all be oriented identically, in which case a single non-rotatable cassette lift is sufficient.

The structure of the cassette lift is described below.

Furthermore, a handling device 100 is provided on the carriage 56. In the embodiment according to FIG. 10 this handling device 100 is arranged between the two cassette lifts 60.

The structure and the function of the handling device 100 correspond essentially to those of the handling device according to WO 02/059251.

The handling device 100 comprises a vertical guide 102, on which a handling carriage 104 is arranged in an automatically moveable manner in the vertical direction. A scoop 106 that can be extended horizontally is provided on the handling carriage 104. The scoop 106 can preferably be pivoted by at least 180° about a vertical axis so that in the embodiment according to FIG. 10 it can optionally be moved into the storage cassettes 20 of the cassette lifts 60 lying opposite one another, and there can take up or deposit a sample plate. Furthermore, it can also be pivoted in the longitudinal direction of the storage arrangement 1 in order to deposit or take up a sample plate at a transfer station 108 (see FIG. 2) arranged at the end in the storage arrangement 1.

A climate controlled cabinet 110 can be provided outside the outer housing at the location of the transfer station 108, which climate controlled cabinet is able to exchange laboratory objects or storage plates with the transfer station 108.

Furthermore, a sample removal device can also be provided on the carriage 56, with which sample removal device it is possible to remove a sample tube from a sample plate removed from a cassette or to add a sample tube to such a plate without the sample plate having to leave the climatic chamber 2. This measure reduces the dwell time of the samples outside the storage temperature and increases the sample throughput by reducing the transport paths. A suitable construction of a sample removal device is disclosed in EP 2078961.

Figure 11:
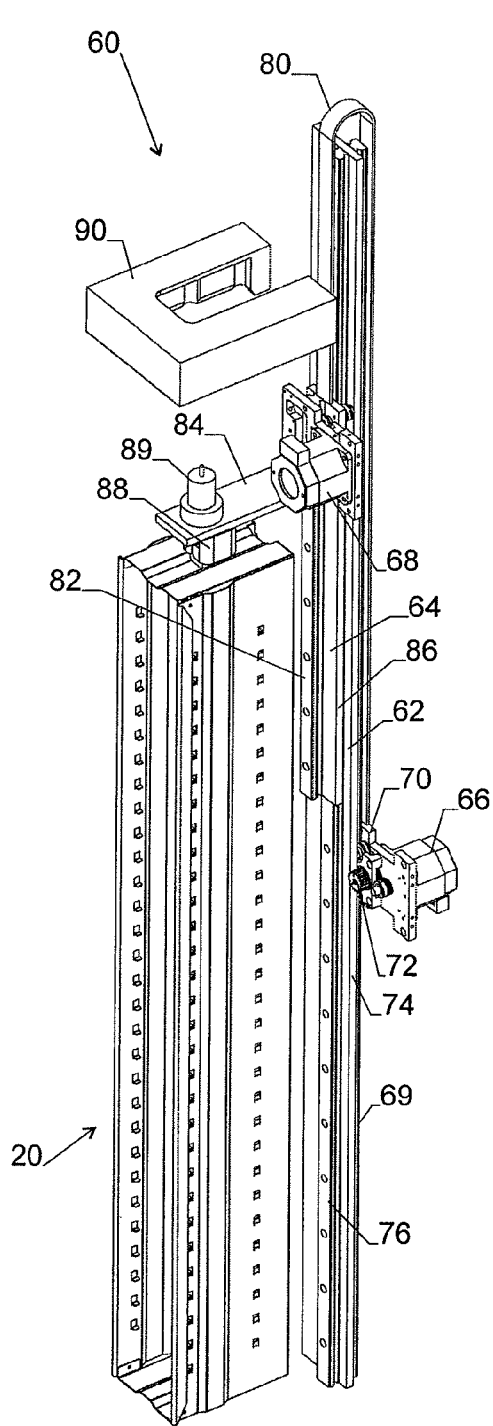
FIG. 11 a first embodiment of a cassette lift.

Cassette Lift:

FIG. 11 shows a first embodiment of a cassette lift. In this embodiment each cassette lift 60 has several telescopic sections 62, 64 that can be extended in a telescopic manner with respect to one another as well as a corresponding number of vertical drives 66, 68.

A first telescopic section 62 is attached to the carriage 56 in a stationary manner. A first vertical rail 69 is arranged on the first telescopic section 62, on which first vertical rail a first vertical drive 66 is arranged in a slidable manner. The vertical drive 66 is connected via a first guide 70 to the first vertical rail 69 and engages with a sprocket 72 in a gear rack 74 on the first telescopic section 62.

Furthermore, a second vertical rail 76 is arranged on the first telescopic section 62, to which second vertical rail the second telescopic section 64 is attached in a vertically moveable manner. It is connected to the first vertical drive 66 via a flexible, strong, low-temperature resistant belt or a chain 80 deflected at the upper end of the first telescopic section 62, so that a lowering or raising of the first vertical drive 66 causes a raising or lowering of the second telescopic section 66 by the same height relative to the first telescopic section 62. Thus the second telescopic section 64 can be extended or retracted in a telescopic manner with the first vertical drive 64.

A third vertical rail 82 is arranged on the second telescopic section 64, on which third vertical rail an arm 84 of the cassette lift 60 is supported in a vertically moveable manner. The second vertical drive 68 is designed to move the arm 84 vertically with respect to the second telescopic section 64. In the embodiment shown in FIG. 11, the second vertical drive 68 to this end engages with a sprocket in a gear rack 86 on the second telescopic section 64.

A gripper device 88 with a gripper drive 89 is arranged on the arm 84, with which gripper drive the handle 36 of a storage cassette 20 can be seized from above.

At least one centering element 90 is provided at a fixed height on the carriage 56 or on the first telescopic section 62 above the gripper device 88, which centering element forms a seat tapering upwards for accommodating a storage cassette 20, when the storage cassette is moved into its uppermost position with the cassette lift 60. Since at the same time the gripper device 88 has some clearance at the side, the centering element 90 defines the horizontal position of the raised storage cassette 20 and thus makes it possible to exactly align the storage cassette horizontally.

Figure 12:
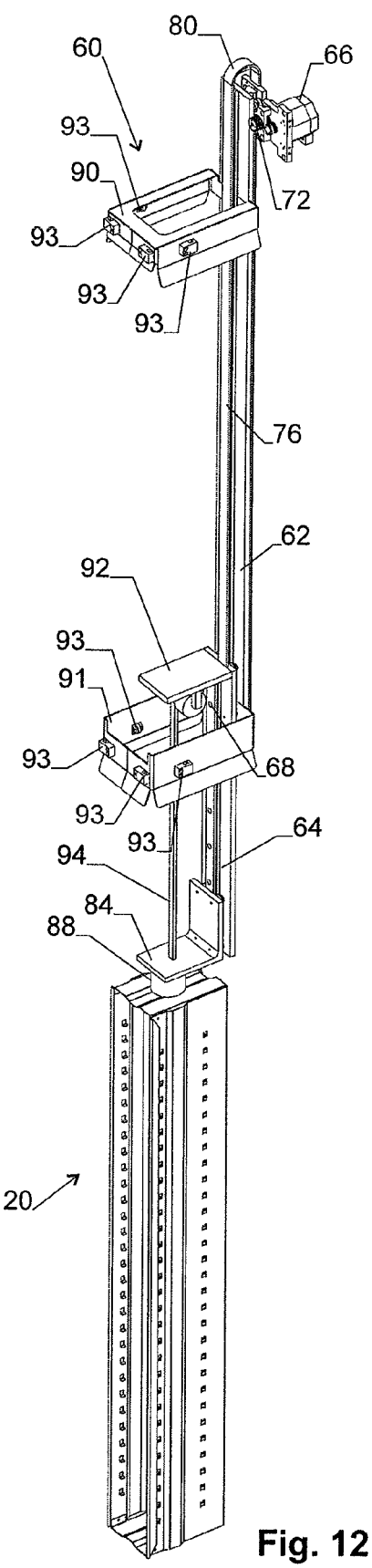
FIG. 12 a second embodiment of a cassette lift in lowered position.
Figure 15:
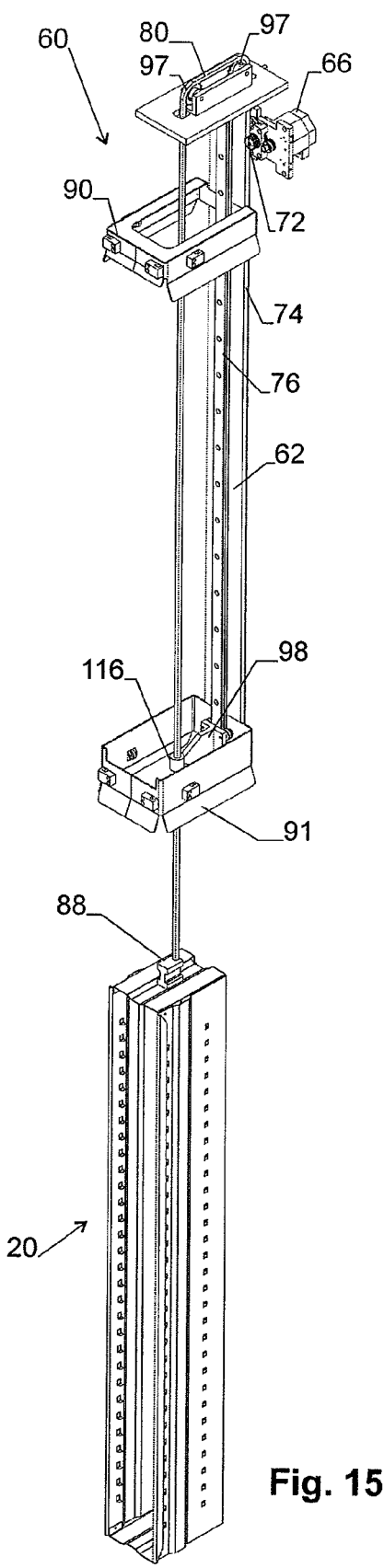
FIG. 15 a third embodiment of a cassette lift in lowered position.
Figure 16:
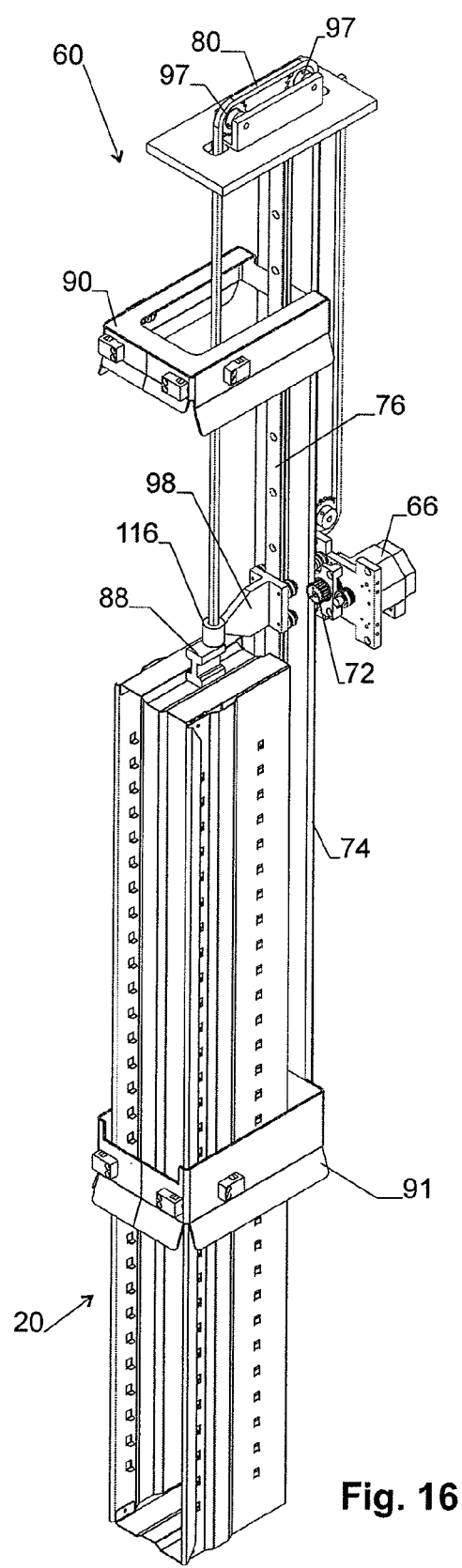
FIG. 16 the cassette lift from FIG. 15 in center position.

FIGS. 12-14 show a second embodiment of a cassette lift 60. It corresponds structurally to that according to FIG. 11, with the following differences:

The second vertical drive 68 is not arranged on the arm 84, but at the upper end 92 of the second telescopic section 64. It forms a reel for a chain 94, at the lower end of which the arm 84 is attached. The arm 84 can thus be raised and lowered by winding and unwinding the chain 94. This solution has the advantage that the second vertical drive can be fixedly attached to the second telescopic section 64 and does not have to be lowered so far down into the low temperature range.

Two centering elements 90, 91 spaced apart vertically from one another are provided. An upper centering element 90 is designed approximately the same as the centering element 90 of the first embodiment and again forms a seat tapering upwards for the storage cassette 20, while the lower centering element 91 forms a collar tapering upwards into which the storage cassette 20 moves when raised. When the storage cassette 20 is raised, the upper centering element 90 comes to rest in the region of the upper end of the storage cassette 20 and the lower centering element 91 comes to rest in the region of the lower end of the storage cassette 20, so that the raised storage cassette 20 is guided horizontally at both ends. In order to ensure a guidance with low friction, spring-mounted roller bearings 93 are provided on the centering elements (FIG. 12).

The gripper device 88 is embodied as an electromagnet.

FIGS. 15-18 show a third embodiment of a cassette lift 60. It corresponds structurally to that according to FIGS. 12-14, with the differences described below.

The third embodiment of the cassette lift is not based on a telescopic arrangement of elements. Instead, the chain 80 together with rollers 96, 97 forms a pulley which is used to lower the gripper device 88 into the Dewar flasks 4. To this end, the chain is deflected over at least one lower and at least one upper roller 96 and 97 respectively, cf. FIG. 18. One of the rollers, advantageously the lower roller 96, can be displaced in the vertical direction via the vertical drive 66, while the other roller and the upper end of the chain 80 are vertically stationary.

In the embodiment shown, the vertical drive is arranged on the first vertical rail 69 of a rail carrier 62 (FIG. 18). The rail carrier 62 corresponds to the first telescopic element 62 of the previous embodiments and is fixedly arranged on the carriage 56.

The chain 80 deflected at the upper end of the cassette lift 60 hangs vertically downwards and bears on its lower end the gripper device 88, which, as in the second embodiment of the cassette lift, is formed by an electromagnet, with which the respective storage cassette can be retained magnetically. (In FIGS. 15-18 the gripper device 88 has by way of example the same form as the handle 36 from FIG. 6, however it forms a separate element from the handle 36. When an electromagnet is used as a gripper device 88, the handle 36 can be omitted, if the storage cassette 20 can be retained at least on its lower end magnetically.)

In order to stabilize the chain 80 laterally somewhat, a guide element 98 is provided, which is guided on a second vertical rail 76 in a longitudinally slidable manner. The second vertical rail 76 is likewise arranged on the rail carrier 62. The guide element 98 forms a lateral guide for the chain 80, preferably an eyelet 116, through which the chain 80 runs. In the lowered position of the storage cassette 20 (cf. FIG. 16), the guide element 98 is located at a stop at the lower end of the second vertical rail 76. When the storage cassette 20 is raised, the eyelet 116 strikes the gripper 88 and is carried along, cf. FIGS. 16-18.

The embodiment according to FIGS. 15-18 also has among other things the advantage that it requires only one vertical drive 66, which furthermore can be arranged relatively high on the lift and does not need to be lowered into the very cold regions of the storage arrangement.

The use of a pulley is furthermore advantageous because it makes it possible to reduce the vertical stroke of the motor and thus the installation height. However, the chain or the belt 80 does not necessarily need to be arranged in a pulley. Instead of a pulley it is also possible e.g. to roll up the belt or the chain 80 on a driven roller or reel, or to unroll it therefrom, as shown in the embodiment for the chain 94 shown in FIGS. 12-14. In this case the gripper device 88 for gripping the storage cassettes 20 can also be lowered on a chain or a belt 80 into the Dewar flasks.

Centering Element in the Dewar Flask

Additionally or alternatively to the centering elements 90 and 91, a centering element 95 can also be provided on the Dewar flask 4', as is shown in FIGS. 20 and 21. Advantageously, this centering element 95 is arranged in the opening 6. As can be seen from FIG. 21, the centering element 95 has an upper collar 96 widening upwards as well as a lower collar 97 widening downwards, which facilitate an introduction of the storage cassette 20 from above or below. It is aligned via lateral feet 98 in the opening 6 in correct position relative to the carousel 18, and it forms at least one guide opening 99, in which the storage cassette is guided horizontally when being drawn out of or inserted into the Dewar flask. A horizontal clearance, which is as low as possible, e.g., no more than 5 mm, remains between the guide opening 99 and a storage tower.

In the embodiment according to FIGS. 20 and 21, the centering element has several guide openings 99, which are arranged at different distances from the rotational axis 16. The distances of the guide openings 99 from the rotational axis 16 correspond to the radii of the circles of the storage towers in the carousel 18.

Remarks:

As shown in FIG. 19, at least one holder element 107, e.g., in the form of a finger, directed upwards, in particular directed obliquely upwards, is preferably arranged on the scoop 106 (cf. FIG. 10), namely at that end of the scoop 106 with which it is moved into the storage cassettes 20. In the embodiment according to FIG. 19, two holder elements 107 of this type are arranged spaced apart from one another. These holder elements 107 are used to secure the laboratory objects on the scoop from the rear, so that they do not fall off the scoop.

The back wall 32 of the storage cassettes 20 is structured such that the holder elements 107 have room to be brought from below behind a laboratory object held in the storage cassette 20. For this purpose the back wall 32, as shown in FIG. 7, is set back in two lateral regions 32a running vertically with respect to their central region 32b. In other words, a first region (central region 32b) of the back wall 32 forms a spacer, with respect to which at least one second region (in FIG. 7 the lateral regions 32a) is set back such that the holder elements 107 can be inserted behind the laboratory objects held in the storage cassette, i.e., that the holder elements 107 have room behind the laboratory object held in the storage cassette. (The term "behind" thereby designates that side of the laboratory objects which faces towards the back wall 32). In the embodiment according to FIG. 19, the second region 32a is set back with respect to the first region 32b, the second region 32a of the back wall can also be omitted, however.

It is mentioned in the above description that the storage arrangement 1 as well as the storage cassettes 20 are used to store sample tubes. However, they are also suitable for storing samples in another form, generally suitable for storing laboratory objects. These can be, e.g., biological or chemical samples. A typical use also relates to the storage of laboratory samples in microtitration plates, in which case the sample plates are embodied as microtitration plates. It is also conceivable that, instead of the sample plates, sample holders, e.g., flasks, are used, which each hold only one sample.

While preferred embodiments of the invention are described in the present application, it should be noted that the invention is not restricted thereto and can also be carried out in another manner within the scope of the following claims.

The invention claimed is:

1. A storage arrangement for storing laboratory objects comprising:
    a chamber;
    at least one Dewar flask positionable in the chamber that is structured and arranged to store the laboratory objects at a storage temperature $Ts<Tc$, in which $Tc$ is a temperature of the chamber;
    a plurality of storage cassettes positionable in the at least one Dewar flask, each storage cassette including a plurality of storage sites arranged one above the other for accommodating the laboratory objects; and
    a picking device structured and arranged for movement in the chamber above the at least one Dewar flask and having at least one cassette lift structured and arranged to selectively remove storage cassettes from the at least one Dewar flask and to place storage cassettes into the at least one Dewar flask;
    at least one centering element comprising several guide openings, each opening for accommodating one storage cassette, the at least one centering element positioned in an opening of the at least one Dewar flask and structured and arranged to receive a selected storage cassette in order to horizontally align the storage cassette.

2. The storage arrangement according to claim 1, wherein the at least one cassette lift is further structured and arranged to selectively remove and place the storage cassettes in a vertical direction.

3. The storage arrangement according to claim 1, further comprising a lid located on a top of the at least one Dewar flask structured and arranged to provide access from above to storage cassettes in the at least one Dewar flask.

4. The storage arrangement according to claim 3, wherein the lid is structured to be opened automatically.

5. The storage arrangement according to claim 1, wherein the chamber is a cooling chamber having a cooling device structured and arranged to produce a chamber temperature $Tc<0°$ C.

6. The storage arrangement according to claim 1, wherein the at least one Dewar flask comprises several Dewar flasks positionable arranged in the chamber, and
    wherein the picking device is common to the several Dewar flasks to selectively remove and place storage cassettes respectively from and into the several Dewar flasks.

7. The storage arrangement according to claim 1, wherein the cassette lift comprises one of a chain or a belt and a gripper device coupled to the one of a chain or belt that is structured and arranged to be lowerable into the at least one Dewar flask and to grip a selected storage cassette.

8. The storage arrangement according to claim 7, wherein the one of a chain or belt is arranged in a pulley.

9. The storage arrangement according to claim 8, wherein the one of a chain or belt is deflected by the pulley, which comprises at least one vertically stationary roller and at least one roller that is displaceable in a vertical direction via a vertical drive.

10. The storage arrangement according to claim 1, wherein the cassette lift comprises an electromagnet structured and arranged as a gripper device to magnetically retain the storage cassettes.

11. The storage arrangement according to claim 1, wherein the cassette lift comprises an additional at least one centering element.

12. The storage arrangement according to claim 1, wherein the picking device comprises a carriage structured and arranged for horizontal movement in two directions, and
    wherein the cassette lift is arranged on the carriage.

13. The storage arrangement according to claim 12, further comprising a first and second rail located within the chamber above the at least one Dewar flask to which the carriage is connectable, the first and a second rail being oriented perpendicular to one another.

14. The storage arrangement according to claim 1, further comprising a housing structured and arranged to surround the chamber.

* * * * *